United States Patent
Levine et al.

(10) Patent No.: US 7,035,687 B1
(45) Date of Patent: Apr. 25, 2006

(54) IMPLANTABLE CARDIAC STIMULATION SYSTEM PROVIDING CAPTURE THRESHOLD STABILITY ASSESSMENT AND METHOD

(75) Inventors: Paul A. Levine, Santa Clarita, CA (US); Jeffrey D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 510 days.

(21) Appl. No.: 10/382,215

(22) Filed: Mar. 4, 2003

(51) Int. Cl.
*A61N 1/24* (2006.01)

(52) U.S. Cl. .................................... 607/28
(58) Field of Classification Search .......... 607/28, 607/9, 32
See application file for complete search history.

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,729,376 A | 3/1988 | DeCote, Jr. | 128/419 PT |
| 4,969,467 A | 11/1990 | Callaghan et al. | 128/419 PG |
| 5,350,401 A * | 9/1994 | Levine | 607/4 |
| 5,350,410 A | 9/1994 | Kleks et al. | 607/28 |
| 6,129,746 A | 10/2000 | Levine et al. | 607/27 |
| 6,243,606 B1 | 6/2001 | Mann et al. | 607/14 |
| 6,259,950 B1 | 7/2001 | Mann et al. | 607/28 |
| 6,285,908 B1 | 9/2001 | Mann et al. | 607/28 |
| 6,317,633 B1 * | 11/2001 | Jorgenson et al. | 607/28 |
| 6,366,812 B1 | 4/2002 | Levine et al. | 607/27 |

FOREIGN PATENT DOCUMENTS

EP  1136098 A2  1/2001

OTHER PUBLICATIONS

Helio Fornieles-Perez et al., "Documentation of Acute Rise in Ventricular Capture Thresholds Associated with Flecainide Acetate," PACE, vol. 25, No. 5, pp 871-872 (May 2002).

* cited by examiner

*Primary Examiner*—Mark Bockelman
*Assistant Examiner*—Joy Patel

(57) ABSTRACT

An implantable cardiac stimulation system provides capture threshold stability assessment. The system includes an implantable pulse generator that provides pacing stimulation pulses, an implantable lead system that couples the pulse generator to a patient's heart, and a capture threshold test circuit that performs capture threshold tests with the pulse generator and provides capture thresholds at spaced apart times. A capture threshold processor responsive to the capture thresholds provides capture threshold stability indicia. The capture threshold stability indicia may be a threshold stability index equal to the ratio of the peak-to-peak threshold fluctuation and the mean capture threshold. The threshold stability index may be compared to a given standard to determine if the capture thresholds are unstable.

36 Claims, 4 Drawing Sheets

IMPLANTABLE CARDIAC STIMULATION SYSTEM PROVIDING CAPTURE THRESHOLD STABILITY ASSESSMENT AND METHOD

FIELD OF THE INVENTION

The present invention generally relates to an implantable cardiac stimulation system that provides electrical therapy to a patient's heart. The present invention more particularly relates to such a system that provides capture threshold stability assessment.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing polarity electrode configurations. In unipolar pacing, the pacing stimulation pulses are applied between a single electrode carried by the lead, in electrical contact with the desired heart chamber, and the pulse generator case. The electrode serves as the cathode (negative pole) and the case serves as the anode (positive pole). In bipolar pacing, the pacing stimulation pulses are applied between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

The energies of the applied pacing pulses must be above the pacing energy stimulation or capture threshold of the respective heart chamber to cause the heart muscle of that chamber to depolarize or contract. If an applied pacing pulse has an energy below the capture threshold of the respective chamber, the pacing pulse will be ineffective in causing the heart muscle of the respective chamber to depolarize or contract. As a result, there will be failure in sustaining the pumping action of the heart. It is therefore necessary to utilize applied pacing pulse energies which are assured of being above the capture threshold.

However, it is also desirable to employ pacing energies which are not exorbitantly above the capture threshold. The reason for this is that pacemakers are implanted devices and rely solely on battery power. Using pacing energies that are too much above the capture threshold represent a waste of energy and result in early battery depletion and hence premature device replacement. Capture thresholds are assessed at the periodic follow-up visits with the physician and the output of the pacemaker is adjusted (programmed) to a safety margin that is appropriate based on the results of that evaluation. However, capture thresholds may change between scheduled follow-up visits with the physician. A refinement of the technique of periodic capture threshold measurement by the physician is the automatic performance of capture threshold assessment (autocapture) and the automatic adjustment of the output of the pulse generator. Capture thresholds may be defined in terms of pulse amplitude, either voltage or current, pulse duration or width, pulse energy, pulse charge or current density. With the introduction of AutoCapture, the implanted pacing system periodically and automatically assesses the capture threshold and then adjusts the delivered output. It also monitors capture on a beat-by-beat basis such that a rise in capture threshold will be immediately recognized allowing the system to compensate. Initially, the compensation is in the form of a significantly higher output back-up or safety pulse and then by incrementing the output of the primary pulse until stable capture is again demonstrated. A pacing energy may then be set by adding a small working margin to the capture threshold to assure reliable pacing without rapid depletion of the battery. Without autocapture, a much larger "safety" margin would have to be set and while this may save some energy for the system, it is not as efficient as AutoCapture with a small working margin and continued monitoring in minimizing battery current drain and maximizing device longevity.

As is well known in the art, the capture threshold of a heart chamber can, for various reasons, change over time. Hence, pacemakers that incorporate autocapture are generally able to periodically and automatically perform autocapture tests. In this way, the variations or changes in capture threshold can be accommodated.

When a pacing pulse is effective in causing depolarization or contraction of the heart muscle, it is referred to as "capture" of the heart. Conversely, when a pacing pulse is ineffective in causing depolarization or contraction of the heart muscle, it is referred to as "lack of capture" or "loss of capture" of the heart.

In one known autocapture test, the pulse generator applies a succession of primary pacing pulses to the heart at a basic rate. To assess the threshold, the output of the primary pulse is progressively reduced. The output of each successive pair of primary pacing pulses is reduced by a known amount and capture is verified following each pulse. If a primary pulse results in loss of capture, a higher output backup or safety pulse is applied to sustain heart activity. If two consecutive primary pulses at the same output level are associated with loss of capture, the system starts to increment the output associated with the primary pulse. The output of successive primary pacing pulses is then incrementally increased until a primary pacing pulse regains capture. The output of the primary pulse which regains capture is the capture threshold to which the safety margin is added in determining the pacing energy. In these methods, capture may be verified by detecting the evoked response associated with the output pulse, the T-waves, mechanical heart contraction, changes in cardiac blood volume impedance, or another signature of a contracting chamber.

There are a number of different reasons why the capture threshold may vary and be unstable. An unstable threshold might indicate, for example, a recently implanted lead which is mechanically unstable. A lead may be mechanically unstable, for example, if it has an insulation or conductor coil failure. Both of these conditions would cause threshold fluctuations. Further, a progressive rise in capture threshold might occur with a developing disease state. Correlation of capture thresholds has not previously been utilized to detect or monitor any of these conditions due to the sporadic nature of the threshold measurements. There is one recent case report in the medical literature (Formieles-Perez H, et al, Documentation of Acute Threshold Rise in Ventricular Capture Thresholds Associated with Flecainide Acetate, PACE 2002; 25.

The present invention addresses this issue. It provides a means by which capture thresholds may be utilized to determine if the capture thresholds are unstable to reveal conditions which may otherwise go unnoticed until further advanced and causing a clinical problem. The capture thresholds may be utilized over short time periods to reveal acute conditions such as mechanical instability of an implanted lead or over longer time periods to reveal chronic conditions such as increasing thresholds associated with disease state or mechanical dysfunction of the chronic pacing lead.

SUMMARY

The invention provides a cardiac stimulation system including an implantable pulse generator that provides pacing stimulation pulses, an implantable lead system that couples the pulse generator to a patient's heart, and a capture threshold test circuit that performs capture threshold tests with the pulse generator and that provides capture thresholds at spaced apart times. The system further includes a capture threshold processor responsive to the capture thresholds that provides capture threshold stability indicia.

The capture threshold test circuit provides a plurality of capture thresholds over a time period. The threshold stability indicia is a threshold stability index equal to the difference between a maximum and minimum capture threshold divided by a mean capture threshold.

The system may further include an external nonimplantable monitor. The monitor may include the capture threshold processor. The system may further include a telemetry link that conveys the capture thresholds from the implantable pulse generator to the external monitor. The external monitor may further include a warning circuit that generates a warning signal when the indicia indicate that the capture thresholds are unstable. Such a warning signal may produce an audible sound or a flag for display on a monitor display.

Alternatively, an implantable cardiac stimulation device may enclose the pulse generator, the capture threshold test circuit and the capture threshold processor together.

The implantable cardiac device may then include a telemetry circuit that transmits the threshold stability indicia to an external monitor.

The implantable cardiac device may include a warning circuit that provides a warning signal when the indicia indicate that the capture thresholds are unstable. The telemetry circuit may then be used for transmitting the warning signal to an external nonimplantable monitor. The implantable cardiac device may further include a patient alert circuit that provides the patient with a perceptible indication when the indicia indicates that the capture thresholds are unstable. The alert circuit may include, for example, a vibrating transducer element for alerting the patient.

The implantable cardiac device may further include an impedance measuring circuit that measures impedance of the lead system when the indicia indicates that the capture thresholds are unstable. The lead system preferably provides a plurality of different pacing electrode configurations including at least one unipolar pacing electrode configuration. The implantable cardiac device may further include a switch that selectively couples the pulse generator to any one of the plurality of pacing electrode configurations and that switches the pulse generator to a unipolar pacing electrode configuration when the measured lead impedance is outside of a given range of impedances. When the capture threshold test circuit is an autocapture circuit that performs autocapture tests, the autocapture circuit may be employed to perform an autocapture test with the pulse generator coupled to the unipolar pacing electrode configuration.

The present invention further provides a cardiac stimulation system including implantable stimulation means for providing cardiac pacing pulses, implantable lead means for coupling the stimulation means to a patient's heart, and capture threshold test means for performing capture threshold tests with the stimulation means and providing capture thresholds at spaced apart times. The system further includes capture threshold processing means responsive to the capture thresholds for providing capture threshold stability indicia.

The present invention still further provides a method of determining capture threshold stability of an implantable cardiac stimulation device coupled to a patient's heart by a lead system. The method includes the steps of performing capture threshold tests with the implantable cardiac stimulation device at spaced times during a time period to provide a plurality of capture thresholds, and determining a capture threshold stability indicia for the time period from the plurality of capture thresholds.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
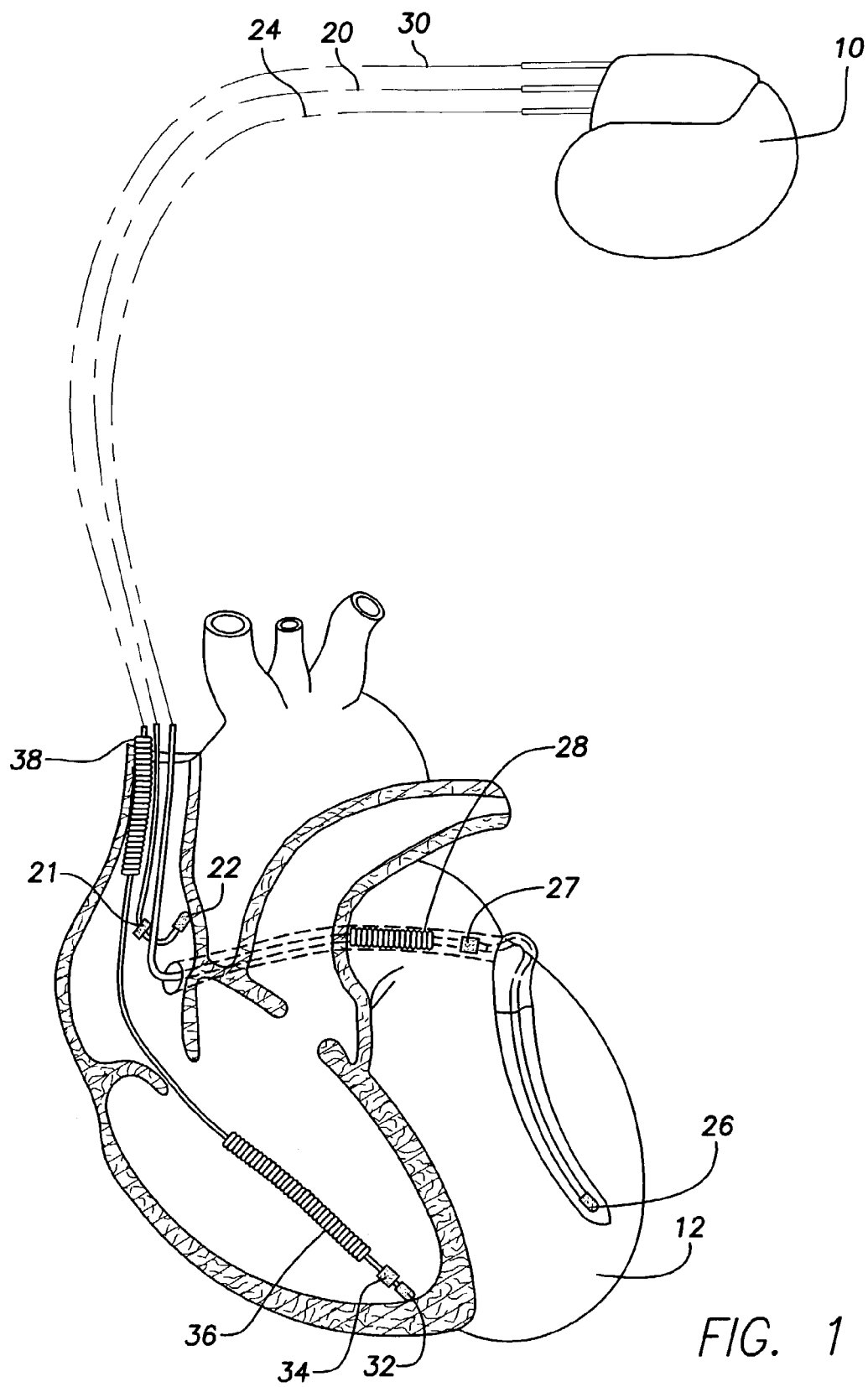
FIG. 1 is a simplified diagram illustrating an implantable cardiac stimulation system embodying the present invention in electrical communication with a patient's heart for delivering multi-chamber stimulation and shock therapy.

As shown in FIG. 1, there is a stimulation system including a device 10 and three leads, 20, 24 and 30, coupling the device to a patient's heart 12 for delivering multi-chamber stimulation and shock therapy. To sense atrial cardiac signals and to provide right atrial chamber stimulation therapy, the stimulation device 10 is coupled to an implantable right atrial lead 20 having an atrial ring electrode 21 and an atrial tip electrode 22, which typically are implanted in the patient's right atrial appendage. The electrodes 21 and 22 may be used as a bipolar electrode pair for bipolar pacing of the right atrium. Alternatively, either electrode 21 or electrode 22 (preferably electrode 22) may be used with the case of the device 10 for unipolar pacing of the right atrium.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. For pacing the right ventricle, the electrodes 32 and 34 may be used together for bipolar pacing or alternatively, either electrode 32 or electrode 34 (preferably electrode 32) may be used with the case of the device 10 for unipolar pacing.

Figure 2:
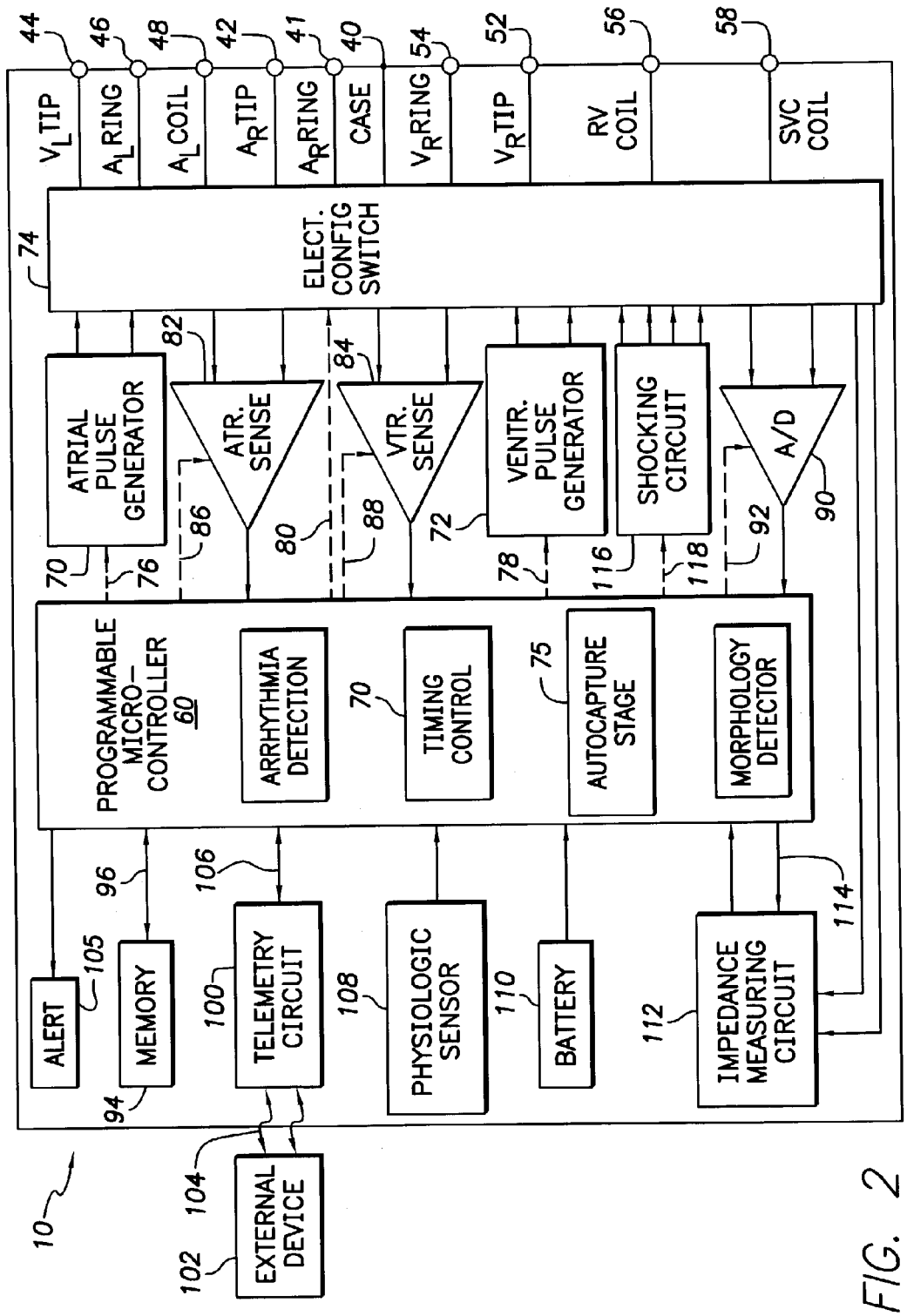
FIG. 2 is a functional block diagram of a multi-chamber implantable stimulation device embodying the present invention illustrating the basic elements thereof for providing cardioversion, defibrillation and pacing stimulation in four chambers of the heart as well as autocapture, capture threshold stability, and lead impedance assessment in accordance with an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes and pacing polarity electrode configurations. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring terminal ($A_R$ RING) 41 adapted for connection to the right atrial ring electrode 21.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control 70 which is used to control the timing of such stimulation pulses (e.g., pacing rate, atrio-ventricular (AV) delay, atrial interconduction (A–A) delay, or ventricular interconduction (V–V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102.

The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, additional elements and functions within the device as they more particularly pertain to this embodiment of the present invention will now be described. The microcontroller includes an autocapture circuit or stage 75. With respect to autocapture, the data acquisition system 90 may be coupled to the microcontroller, or other detection circuitry, for detecting an evoked response from the heart 12 during a window following a stimulation pulse. The presence of an evoked response indicates that capture has occurred. The autocapture 75 enables capture detection by triggering the appropriate pulse generator (ventricular or atrial) to generate a stimulation pulse, starting a capture detection window using the timing control circuitry 70 within the microcontroller 60, and enabling the data acquisition system 90 via control signal 92 to sample the cardiac signal that falls in the capture detection window and, based on the amplitude, determines if capture has occurred.

In accordance with this embodiment, a capture threshold search is preferably performed at spaced apart times, such as every eight hours, or more frequently if required. More frequent capture threshold searching may be desirable when, for example, the capture thresholds are found to be unstable. A capture threshold search would begin with a small increase in pacing rate and at a desired starting primary pacing pulse energy sufficient to assure initial capture. The energies of subsequent primary pacing pulses are then decreased until capture is lost. When capture is lost, the primary pacing pulse is followed, fifty to one-hundred milliseconds thereafter, by a backup pacing pulse at a higher energy to assure capture and contraction of the heart chamber. Thereafter, the energies of subsequent primary pacing pulses are incrementally increased. Again, backup pulses are provided if a primary pacing pulse does not result in capture. The energy of the first increased primary pacing pulse to regain capture is known as the capture threshold. Hence, each autocapture search results in a determined capture threshold. Thereafter, to complete an autocapture assessment, a working margin is added to the capture threshold to determine the next regular pacing energy.

The implementation of capture detection circuitry and algorithms is well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

After each autocapture search, the determined capture threshold is stored in the memory 94. In accordance with one embodiment, and as will be described with reference to FIG. 3 hereinafter, the stored capture thresholds may be transmitted to the external device 102, which may be an external programmer or monitor, over the telemetry link 104 for further processing to derive capture stability indicia in accordance with the present invention. Alternatively, the stored capture thresholds may be utilized by the microcontroller 60 of the device 10 for deriving the capture stability indicia. The device 10 may derive the capture stability indicia at spaced apart or periodic times such as each day for short term indicia or each week for long term indicia. Each indicia will provide a measure of capture threshold stability over the time period since the last capture stability assessment.

In accordance with this embodiment, the capture stability indicia is a threshold stability index equal to the difference between the maximum capture threshold determined during the given time period and the minimum capture threshold determined during the given time period or peak-to-peak threshold fluctuation (PPTF) divided by the mean capture threshold (MCT) for the given time period. Once the threshold stability index (TSI) is determined, it may be compared to a given standard to determine if the TSI indicates that the capture thresholds are unstable. For example, if the TSI is less than 0.5, the capture thresholds are considered stable and if the TSI is greater than 1.0, the capture thresholds are considered to be stable. As a realistic example, a peak-to-peak threshold fluctuation (PPTF) of 0.25 V together with a MCT of 0.75 V renders a stable TSI of 0.33. However, a PPTF of 1.0 V together with a MCT of 0.75 V would render an unstable TSI of 1.33.

If the TSI is determined in the implantable device, it may be stored in the memory 94. Thereafter, at follow-up visits to the physician, the TSI's may be transmitted to the external device 102 for display. Further, the device 10 includes a patient alert 105 which may alert the patient of a TSI considered to indicate unstable capture thresholds. The alert 105 may be, for example, a transducer element which vibrates and which may be discerned by the patient. Still further, when a TSI occurs that is considered to indicate unstable capture thresholds, the microcontroller 60 may set a flag in memory 94 to immediately alert the physician when the telemetry transmits to the external device 102 at follow-up.

As further shown in FIG. 2, and in accordance with the present invention, the device 10 includes an impedance measuring circuit 112 which is enabled by the microcontroller 60 via a control signal 114. In accordance with this embodiment of the present invention the impedance measuring circuit is enabled whenever there is a TSI indicating unstable capture thresholds and possibly a mechanical lead failure. Hence, the impedance measuring circuit 112 measures the lead impedance of the then current pacing electrode configuration. The impedance measuring circuit 112 is advantageously coupled to the switch 74 so that the impedance of any available pacing electrode configuration may be measured.

If the measured impedance falls outside of a given impedance range, as for example 50 to 200 ohms, indicating a lead failure, the impedance measuring circuit 112, through the microcontroller 60, will cause the switch 74 to switch the pacing electrode configuration to a unipolar pacing electrode configuration. The microcontroller 60 will then cause the autocapture 75 to conduct an autocapture test with the unipolar pacing electrode configuration. In completing the unipolar capture test, the autocapture 75 adds the safety margin to the determined capture threshold and then enables continued pacing in the unipolar pacing electrode configuration.

Figure 3:
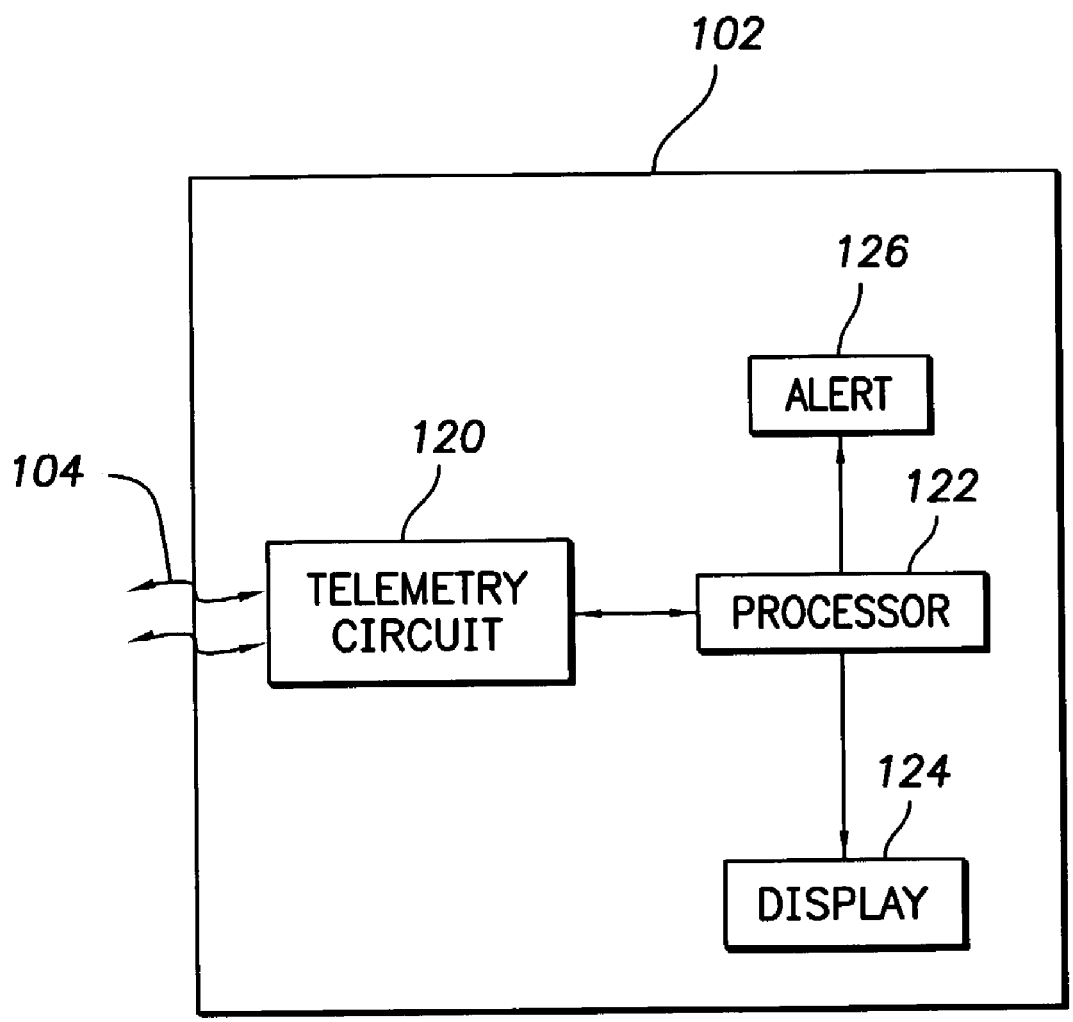
FIG. 3 is a simplified block diagram of an external monitor embodying the present invention.

FIG. 3 shows a simplified block diagram of the external device 102 when the external device is an external monitor or programmer which calculates the TSI for display. To that end, the external device 102 includes a telemetry circuit 120 for receiving the capture thresholds and other data from the implantable device 10 over the telemetry link 104. The external device 102 further includes a processor 122 which determines the TSI for each time period. The TSI's may then be displayed on a display 124.

The external device 102 may further include an alert 126 which generates an alert signal when a TSI is determined which is considered to indicate unstable capture thresholds. The alert signal may, for example, be an audible tone to prompt the physician to display the TSI data on the display 124 and take other action such as measuring the impedance of the current pacing electrode configuration.

Figure 4:
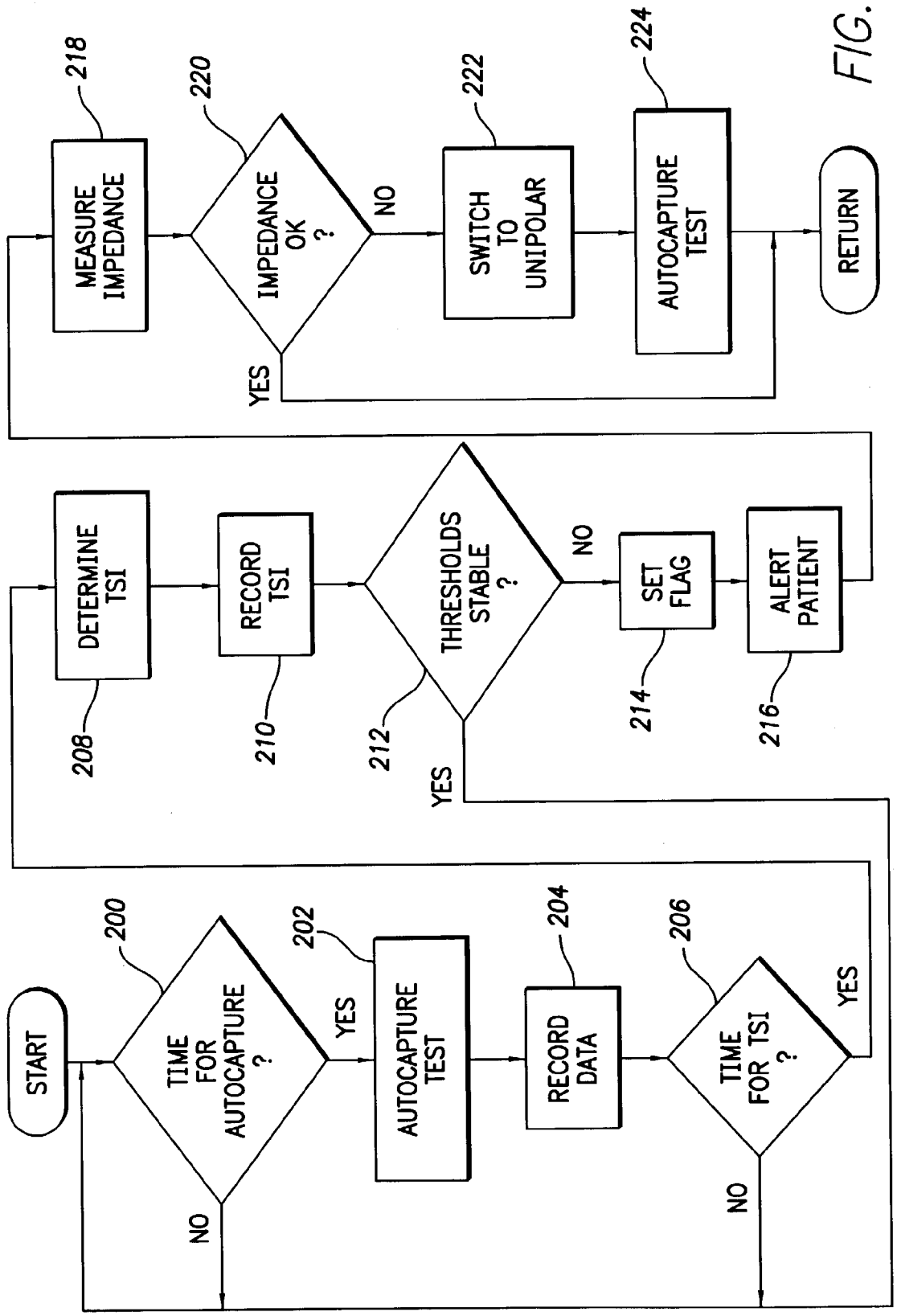
FIG. 4 is a flow chart describing an overview of the operation of one embodiment of the present invention.

In FIG. 4, a flow chart is shown describing an overview of the operation and novel features implemented in the embodiment wherein the device 10 itself determines the TSI for each time period and takes other appropriate action automatically. In this flow chart, the various algorithmic steps are summarized in individual "blocks". Such blocks describe specific actions or decisions that must be made or carried out as the algorithm proceeds. Where a microcontroller (or equivalent) is employed, the flow chart provides the basis for a "control program" that may be used by such a microcontroller (or equivalent) to effectuate the desired control of the stimulation device. Those skilled in the art may readily write such a control program based on the flow charts and other descriptions presented herein.

The process of FIG. 4 begins with decision block 200. In decision block 200, the microcontroller 60 determines if it is time for conducting an autocapture test. If it is not, the process returns. However, if it is time to conduct an autocapture test, the microcontroller 60 through the autocapture 75 causes an autocapture test to be performed in accordance with activity block 202. Once the autocapture test is performed, the process advances to activity block 204 wherein the capture threshold determined during the autocapture test is stored in memory 94.

After the capture threshold is stored in memory 94, the process advances to decision block 206 wherein the microcontroller 60 determines if it is time to determine a threshold stability index (TSI). If it is not time to determine a TSI, the process returns. However, if it is time to determine a TSI, the process advances to activity block 208. In activity block 208, the TSI is determined as previously described. More specifically, the microcontroller determines the ratio between the peak-to-peak threshold fluctuation (PPTF) and the mean capture threshold (MCT). As previously mentioned, the TSI may be determined daily if short term threshold stability is of concern or weekly if long term stability is of concern. Short term stability may be of concern after initial implant of the implantable cardiac stimulation system to monitor mechanical stability of the lead system or if a TSI indicated unstable capture thresholds. Long term threshold stability may be of concern when monitoring disease state of a patient or continued mechanical integrity of the lead. In either event, the autocapture test is performed at more frequent intervals in order to generate sufficient data to determine a maximum capture threshold, a minimum capture threshold, and a mean capture threshold.

Once the TSI is determined in accordance with activity block 208, the process advances to activity block 210 wherein the TSI is stored in memory 94. The TSI is stored in memory 94 for later transmission to the external device 102 during follow-up, for example.

After the TSI is stored in memory, the process advances to decision block 212 wherein the microcontroller determines if the TSI indicates if the capture thresholds are stable. If the microcontroller determines that the capture thresholds are stable, the process returns. However, if the TSI indicates that the capture thresholds are unstable, the process immediately advances to activity block 214 for setting a flag in memory. The flag set in memory enables the device to alert the physician upon telemetry interrogation of the device by the physician's external programmer or monitor. After the flag is set, the process advances to activity block 216 wherein the patient is alerted. Here, the alert 105 provides the patient with a perceptible indication that the TSI indicated unstable capture thresholds. As previously mentioned, the alert may take the form of a vibrating transducer which causes the device to create a vibration discernable by the patient. The patient, now being alerted, may contact suitable medical personnel for immediate follow-up allowing a more detailed evaluation.

Once the patient is alerted in accordance with activity block 216, the process then advances to activity block 218 wherein the impedance measuring circuit 112 measures the impedance of the current pacing electrode configuration. Once the impedance of the current pacing electrode configuration is determined, the process advances to decision block 220 wherein the microcontroller determines if the measured impedance falls within a given range. As previously mentioned, the given range may be between 50 and 200 ohms. If the impedance is within the given range, the process returns. However, if the impedance is outside of the given range, indicating a potential mechanical failure of the implanted lead, the process then advances to activity block 222 wherein the switch 74 is caused to switch the device to a unipolar pacing electrode configuration. Once the device is coupled to a unipolar pacing electrode configuration in accordance with activity block 222, the process advances to activity block 224 wherein the autocapture 75 performs an autocapture test with the device now coupled to the unipolar pacing electrode configuration. The autocapture test is performed in accordance with activity block 224 to assure sufficient pacing energies for capturing the heart. Once the autocapture test is completed in accordance with activity block 224, the process returns.

In one illustrative embodiment, the TSI can be used to control the safety margin added to the capture threshold value to determine the pacing energy. For example, if the TSI is found to be unstable, the system may use a relatively large safety margin, whereas if the TSI is stable, then a conventional, relatively small safety margin may be used.

While the invention has been described by means of specific embodiments and applications thereof, it is understood that numerous modifications and variations could be made thereto by those skilled in the art without departing from the spirit and scope of the invention. For example, the capture threshold stability and lead impedance assessment provided by the present invention may be carried out with pacing electrode configurations for pacing any one of the right atrium, left atrium, right ventricle, or left ventricle. It is therefore to be understood that within the scope of the claims, the invention may be practiced otherwise than as specifically described herein.

The invention claimed is:
1. A cardiac stimulation system comprising:
an implantable pulse generator that provides pacing stimulation pulses;
an implantable lead system that couples the pulse generator to a patient's heart;

a capture threshold test circuit that performs capture threshold tests with the pulse generator and that determines capture thresholds at spaced apart times; and a capture threshold processor responsive to the capture thresholds that determines capture threshold stability indicia;

wherein the capture threshold stability indicia is a function of a peak-to-peak threshold fluctuation and a mean capture threshold.

2. The system of claim 1 wherein the capture threshold test circuit provides a plurality of capture thresholds over a time period and wherein the threshold stability indicia is a threshold stability index equal to the difference between a maximum and minimum capture threshold divided by a mean capture threshold.

3. The system of claim 1 further comprising an implantable cardiac stimulation device that includes the pulse generator, the capture threshold test circuit and the capture threshold processor.

4. The system of claim 3 wherein the implantable cardiac device further includes a telemetry circuit that transmits the threshold stability indicia to an external monitor.

5. The system of claim 3 wherein the implantable cardiac device includes a warning circuit that provides a warning signal when the indicia indicate that the capture thresholds are unstable.

6. The system of claim 5 wherein the implantable cardiac device includes a telemetry circuit for transmitting the warning signal to an external nonimplantable monitor.

7. The system of claim 3 wherein the implantable cardiac device includes a patient alert circuit that provides the patient with a perceptible indication when the indicia indicates that the capture thresholds are unstable.

8. The system of claim 3 wherein the implantable cardiac device further includes an impedance measuring circuit that measures impedance of the lead system when the indicia indicates that the capture thresholds are unstable.

9. The system of claim 8 wherein the lead system provides a plurality of different pacing electrode configurations including at least one unipolar pacing electrode configuration, wherein the implantable cardiac device includes a switch that selectively couples the pulse generator to any one of the plurality of pacing electrode configurations, and wherein the switch couples the pulse generator to a unipolar pacing electrode configuration when the measured lead impedance is outside of a given range of impedances.

10. The system of claim 9 wherein the capture threshold test circuit is an autocapture circuit that performs autocapture tests and wherein the autocapture circuit performs an autocapture test with the pulse generator coupled to the unipolar pacing electrode configuration.

11. A cardiac stimulation system comprising:
an implantable pulse generator that provides pacing stimulation pulses;
an implantable lead system that couples the pulse generator to a patient's heart;
a capture threshold test circuit that performs capture threshold tests with the pulse generator and that determines capture thresholds at spaced apart times;
a capture threshold processor responsive to the capture thresholds that determines capture threshold stability indicia; and
an external nonimplantable monitor including the capture threshold processor and a telemetry link that conveys the capture thresholds from the implantable pulse generator to the external monitor.

12. The system of claim 11 wherein the external monitor further includes a warning circuit that generates a warning signal when the indicia indicate that the capture thresholds are unstable.

13. A cardiac stimulation system comprising:
implantable stimulation means for providing cardiac pacing pulses;
implantable lead means for coupling the stimulation means to a patient's heart;
capture threshold test means for performing capture threshold tests with the stimulation means and determining capture thresholds at spaced apart times; and
capture threshold processing means responsive to the capture thresholds for determining capture threshold stability indicia;
wherein the capture threshold stability indicia is a function of a peak-to-peak threshold fluctuation and a mean capture threshold.

14. The system of claim 13 wherein the capture threshold test means provides a plurality of capture thresholds over a time period and wherein the threshold stability indicia is a threshold stability index equal to the difference between a maximum and minimum capture threshold divided by a mean capture threshold.

15. The system of claim 13 further comprising implantable enclosure means for enclosing the stimulation means, the capture threshold test means and the capture threshold processor means.

16. The system of claim 15 wherein the enclosure means further includes telemetry means for transmitting the threshold stability indicia to an external monitor.

17. The system of claim 15 wherein the enclosure means includes a warning circuit that provides a warning signal when the indicia indicate that the capture thresholds are unstable.

18. The system of claim 17 wherein the enclosure means includes a telemetry circuit for transmitting the warning signal to an external nonimplantable monitor.

19. The system of claim 15 wherein the enclosure means includes patient alert means for providing the patient with a perceptible indication when the indicia indicates that the capture thresholds are unstable.

20. The system of claim 15 wherein the enclosure means further includes impedance measuring means for measuring impedance of the lead means when the indicia indicates that the capture thresholds are unstable.

21. The system of claim 20 wherein the lead means provides a plurality of different pacing electrode configurations including at least one unipolar pacing electrode configuration, wherein the enclosure means includes switch means for selectively coupling the stimulation means to any one of the plurality of pacing electrode configurations, and wherein the switch means couples the stimulation means to a unipolar pacing electrode configuration when the measured lead impedance is outside of a given range of impedances.

22. The system of claim 21 wherein the capture threshold test means is an autocapture circuit that performs autocapture tests and wherein the autocapture circuit performs an autocapture test with the stimulation means coupled to the unipolar pacing electrode configuration.

23. A cardiac stimulation system comprising:
implantable stimulation means for providing cardiac pacing pulses;
implantable lead means for coupling the stimulation means to a patient's heart;

capture threshold test means for performing capture threshold tests with the stimulation means and determining capture thresholds at spaced apart times;

capture threshold processing means responsive to the capture thresholds for determining capture threshold stability indicia; and external monitor means including the capture threshold processor for providing the capture threshold stability indicia and telemetry means for conveying the capture thresholds from the implantable stimulation means to the external monitor means.

24. The system of claim 23 wherein the external monitor means further includes warning means for providing a warning signal when the indicia indicate that the capture thresholds are unstable.

25. A method of determining capture threshold stability of an implantable cardiac stimulation device coupled to a patient's heart by a lead system, the method comprising:

performing capture threshold tests with the implantable cardiac stimulation device at spaced times during a time period to derive a plurality of capture thresholds; and determining a capture threshold stability indicia for the time period from the plurality of capture thresholds;

wherein the capture threshold stability indicia is a function of a peak-to-peak threshold fluctuation and a mean capture threshold.

26. The method of claim 25 wherein the capture threshold stability indicia is a capture stability index equal to the ratio of the difference between a maximum capture threshold and a minimum capture threshold and a mean capture threshold.

27. The method of claim 25 wherein determining is performed by the implantable cardiac stimulation device and further comprising transmitting the capture threshold stability indicia to an external, nonimplantable, monitor.

28. The method of claim 27 further comprising causing the implantable cardiac stimulation device to provide a warning signal when a capture threshold stability indicia indicates that the capture threshold are unstable.

29. The method of claim 28 further comprising transmitting the warning signal from the implantable cardiac stimulation device to the external monitor.

30. The method of claim 27 further comprising generating an indication, perceptible by the patient, with the implantable cardiac stimulation device when the capture threshold stability indicia indicate that the capture thresholds are unstable.

31. The method of claim 25 further comprising measuring lead system impedance when a capture threshold stability indicia indicates that the capture thresholds are unstable.

32. The method of claim 31 wherein measuring is performed by the implantable cardiac stimulation device.

33. The method of claim 31 wherein the lead system provides a plurality of different pacing electrode configurations including at least one unipolar pacing electrode configuration and wherein the method further comprises coupling the implantable cardiac stimulation device to a unipolar pacing electrode configuration when the measured lead impedance is outside of a given range of impedances.

34. The method of claim 33 further comprising conducting an autocapture test with the implantable cardiac stimulation device coupled to the unipolar pacing electrode configuration.

35. A method of determining capture threshold stability of an implantable cardiac stimulation device coupled to a patient's heart by a lead system, the method comprising:

performing capture threshold tests with the implantable cardiac stimulation device at spaced times during a time period to derive a plurality of capture thresholds; and determining a capture threshold stability indicia for the time period from the plurality of capture thresholds; and transmitting the capture threshold from the implantable cardiac stimulation device to an external, nonimplantable monitor and wherein the determining step is performed by the external monitor.

36. The method of claim 35 further comprising generating a warning signal with the external monitor when a capture stability indicia indicates that the capture thresholds are unstable.

* * * * *